US008997285B2

(12) United States Patent
Moore

(10) Patent No.: US 8,997,285 B2
(45) Date of Patent: Apr. 7, 2015

(54) ARM PROTECTOR HEAD REST

(75) Inventor: Philip Moore, Seaford (GB)

(73) Assignees: Phillip Moore (GB); James Moore (GB)

(*) Notice: Subject to any disclaimer, the term of this patent is extended or adjusted under 35 U.S.C. 154(b) by 0 days.

(21) Appl. No.: 14/235,913

(22) PCT Filed: Jul. 27, 2012

(86) PCT No.: PCT/GB2012/000621
§ 371 (c)(1),
(2), (4) Date: Oct. 20, 2014

(87) PCT Pub. No.: WO2013/017817
PCT Pub. Date: Feb. 7, 2013

(65) Prior Publication Data
US 2015/0040321 A1 Feb. 12, 2015

(30) Foreign Application Priority Data

Jul. 29, 2011 (GB) .................................. 1113055.6

(51) Int. Cl.
A47G 9/10 (2006.01)
A47G 9/02 (2006.01)

(52) U.S. Cl.
CPC .............. A47G 9/10 (2013.01); A47G 9/0253 (2013.01); A47G 2009/1018 (2013.01); A47G 9/1081 (2013.01); A47G 9/109 (2013.01)

(58) Field of Classification Search
CPC .............. A47G 9/10; A47G 9/1009; A47G 2009/1018; A47G 9/1081; A47G 9/109; A47C 7/383; A47C 20/02; A47C 20/00
USPC ............. 5/636, 643, 646, 642, 632, 630, 652, 5/655.7, 655.9, 953; D6/601
See application file for complete search history.

(56) References Cited

U.S. PATENT DOCUMENTS 3,883,906 A * 5/1975 Sumpter ........................... 5/632
4,821,355 A * 4/1989 Burkhardt ......................... 5/636
(Continued)

FOREIGN PATENT DOCUMENTS

DE 9300619 U1 3/1993

OTHER PUBLICATIONS

International Search Report for International Application PCT/GB2012/000621, dated Nov. 27, 2012.

Primary Examiner — Robert G Santos
(74) Attorney, Agent, or Firm — Lisa M. Warren, Esq.; Morse, Barnes-Brown & Pendleton, P.C.

(57) ABSTRACT

A head rest (10) comprises a curved sheet member (12) having an upper surface (14), a lower surface (16), and front and rear ends (18, 20), wherein the upper surface (14) comprises a generally forwardly facing portion (26) and a generally rearwardly facing portion (28), and wherein the generally forwardly facing portion (26) includes a first concave portion (34) for receiving the head of a user, the front and rear ends (18, 20) are configured for contact with a resting surface (38) and, between the front and rear ends (18, 20), the lower surface (16) defines a passageway (36) dimensioned to receive at least one arm of the user. The head rest has sufficient rigidity such that when the user's head is resting on the member (12), one or both arms of the user may be positioned in the passageway (36) in a manner that does not require the arm(s) to support the weight of the head. In this way, the head rest allows comfortable resting without loss of circulation in the arms.

14 Claims, 2 Drawing Sheets

(56) References Cited

U.S. PATENT DOCUMENTS

| | | |
|---|---|---|
| 5,579,551 A | 12/1996 | Tommaney |
| 5,644,809 A * | 7/1997 | Olson ................................ 5/636 |
| D407,256 S * | 3/1999 | Backlund ....................... D6/601 |
| 6,079,066 A * | 6/2000 | Backlund ......................... 5/636 |
| 6,336,236 B1 * | 1/2002 | Dalton .............................. 5/636 |
| D471,050 S * | 3/2003 | Haubner ........................ D6/601 |
| D484,727 S * | 1/2004 | Haywood ...................... D6/601 |
| 6,671,907 B1 * | 1/2004 | Zuberi ............................. 5/636 |
| 6,691,353 B2 * | 2/2004 | Fuhriman ......................... 5/646 |
| 7,216,387 B2 * | 5/2007 | Laxton ............................. 5/636 |
| 7,228,580 B2 * | 6/2007 | Dalton ............................. 5/636 |
| 7,441,293 B1 * | 10/2008 | Singer et al. ..................... 5/646 |
| 8,069,515 B1 * | 12/2011 | Tingey ............................. 5/632 |
| 8,806,684 B1 * | 8/2014 | Ortega et al. .................... 5/636 |
| 2003/0014820 A1 * | 1/2003 | Fuhriman ......................... 5/646 |
| 2003/0135927 A1 | 7/2003 | Hsia |
| 2006/0200908 A1 * | 9/2006 | Dalton ............................. 5/632 |
| 2006/0282952 A1 * | 12/2006 | Laxton ............................. 5/636 |
| 2011/0296615 A1 * | 12/2011 | Tingey ............................. 5/632 |

* cited by examiner

ARM PROTECTOR HEAD REST

This application is a national stage filing under 35 U.S.C. 371 of International Application No. PCT/GB2012/000621, filed Jul. 27, 2012, which claims priority to GB Application 1113055.5, filed Jul. 29, 2011. The entire teachings of PCT/GB2012/000621 are incorporated herein by reference. International Application PCT/GB2012/000621 was published under PCT Article 21(2) in English.

The present invention relates to devices on which to rest a person's head, such as a pillow. More particularly, the present invention relates to a head rest which protects a user's arm when placed under the head rest and allows the user to sleep or rest with an arm underneath his or her head without disrupting the circulation of blood through the arm.

There are currently in use various devices on which a person may rest their head when sleeping or otherwise relaxing. The most common of these is the traditional pillow which consists of a suitable padding or filling enclosed within a textile case.

When sleeping or resting on one's front or side, it is generally more comfortable to position one or both arms underneath the head or pillow. However, a problem with this position is loss of blood circulation in the arms due to the weight of the head, resulting in paresthesia, which in turn interrupts sleep.

Although there are various known pillows designed to address the aforementioned loss of circulation in the arm during sleep or other activities, such pillows are often oddly shaped and do not allow a user to sleep comfortably.

One object of the present invention is to provide an improved head rest of the type which allows an arm to be placed under a user's resting head such that the head does not require the arm to support the weight of the head.

The present invention accordingly provides a head rest comprising a sheet member having an upper surface, a lower surface, and front and rear ends, the upper surface comprising a generally forwardly facing portion and a generally rearwardly facing portion, wherein the generally forwardly facing portion includes a first concave portion for receiving the head of a user, the front and rear ends are configured for direct or indirect contact with a resting surface and, between the front and rear ends, the lower surface defines a passageway dimensioned to receive at least one arm of the user, wherein the member has sufficient rigidity such that when the user's head is resting on the member, the user's arm may be positioned in the passageway in a manner that does not require the arm to support the weight of the head.

The head rest according to the present invention allows a user to sleep or rest on his or her front or side having one or both arms in a natural position under the head rest without interruption from pressure on, or loss of circulation in, the user's arms.

The head rest according to the present invention is particularly suitable for individuals pre-disposed to snoring as it allows a user to sleep comfortably on his or her front or side while maintaining the head and neck in a proper alignment position such that snoring is prevented or at least reduced. Therefore, the quality of sleep and health of the user is improved.

In a preferred embodiment of the head rest according to the present invention, the front end of the sheet member extends forwardly in the same plane as the resting surface. Preferably also, the rear end of the sheet member extends rearwardly in the same plane as the resting surface.

In one embodiment of the head rest according to the present invention, a second concave portion is provided in the generally rearwardly facing portion of the head rest. Preferably, the radius of curvature of the first concave portion in the generally forwardly facing portion is greater than the radius of curvature of the second concave portion in the generally rearwardly facing portion of the head rest.

Preferably, the first and/or second concave portion is resiliently flexible and configured to flex when a user's head is applied to the forwardly facing portion of the head rest.

The front end of the sheet member preferably gently curves upwardly towards the passageway. The initial angle of inclination of the sheet member from the front end towards the passageway is up to about 30 degrees, preferably from about 5 degrees to about 20 degrees to the horizontal. The rear end of the sheet member also curves upwardly towards the passageway but preferably at a greater angle than the front end. The initial angle of inclination of the sheet member from the rear end towards the passageway is up to about 40 degrees, preferably from about 10 degrees to about 30 degrees to the horizontal. These curved portions of the member are resiliently flexible and configured to flex downwardly when a user's head is resting on the body. When a user's head is applied to the head rest, the initial upwardly inclined portions of the front and/or rear ends of the sheet member flex downwardly to contact, or lie in the same plane as the resting surface. In addition to providing improved comfort and stability, this feature ensures that the load on the resting surface is distributed over a relatively large area, limiting wear and tear of the resting surface.

In a preferred embodiment of the head rest according to the present invention, the sheet member is configured such that a user's head resting on the first concave portion in the forwardly facing portion is not directly above the user's arm in the passageway. Thus, the centre of mass of the user's head and the centre of mass of the user's forearm may lie in different vertical planes, with the user's arm being closer to the rear end of the head rest and the user's head being closer to the front end of the head rest.

The passageway is preferably dimensioned to allow a certain degree of freedom of movement of an arm within it. Ideally, the passageway is dimensioned to accommodate two arms simultaneously.

The sheet member may be made from any suitable material that is relatively rigid yet resilient. Preferably, the sheet member is made from a single piece of material. More preferably, the sheet member is made from moulded plastic.

The thickness of the sheet material will, of course, vary depending upon the material used. Preferably, the sheet material has a thickness of up to about 50 mm, more preferably from about 2 mm to about 40 mm, even more preferably from about 10 mm to about 20 mm.

The head rest according to the present invention may further comprise a cover of a cushioning material over the sheet member. The cushioning material is preferably a foam material such as urethane foam having a compression density that is sufficient to cushion the head of an individual utilizing the head rest.

The cushioning, e.g., foam, material covers at least the forwardly facing upper surface of the sheet material. In a preferred embodiment, the entire upper surface of the sheet material is covered with the cushioning material. The cushioning material is suitably thicker on the forwardly facing upper surface of the head rest, especially on the first concave portion, than elsewhere. The lower surface of the sheet member may also be covered with a suitable material. The foam material covering the upper surface of the sheet material preferably has a thickness of from about 20 mm to about 90 mm in the region where the head is applied and of from about 1 mm to less than about 20 mm elsewhere.

In a preferred embodiment, both upper and lower surfaces of the body are covered with foam material. Suitably, the foam material on the upper surface is of a relatively lower density than the foam material on the lower surface to provide a more cushioning surface. The foam material is secured to the body by any convenient means, generally by glueing.

The head rest may further comprise a removable fabric cover that generally encloses the head rest. The head rest is preferably of a design which accommodates a standard pillow case. Alternatively, the cover is adapted to be fitted to the head rest.

The head rest according to the present invention preferably has a width and length similar to that of a standard pillow. Preferably, the head rest has a length, from the front edge to the rear edge, of from about 350 mm to about 800 mm, more preferably of between about 420 mm and about 700 mm, even more preferably of between about 460 mm and about 550 mm, and has a width of from about 350 mm to about 800 mm, more preferably of between about 400 mm and about 650 mm, even more preferably of between about 420 mm and about 500 mm.

The upper surface of the sheet member extends to a height above the resting surface that is preferably from about 80 mm to about 200 mm, more preferably from about 90 mm to about 150 mm. The height of the passageway is at least 80 mm, preferably up to about 190 mm, more preferably from about 100 to about 140 mm, above the resting surface. The length of the passageway extends from one side edge to the other side edge of the head rest and therefore corresponds to the width of the head rest. The width of the passageway itself is preferably at least sufficient to accommodate two arms of a user side by side.

The head rest of the present invention allows a user to sleep or rest on his or her front or side having one or both arms in position under the head rest while reducing pressure and loss of circulation to the user's arms. By allowing the user to sleep comfortably on his or her front or side, snoring can be prevented or at least reduced.

Further, the head rest according to the present invention allows a user to adjust the position of his or her arm or arms below the user's resting head without the user having to adjust the position of his or her resting head.

Additionally, the head rest according to the present invention maintains the head and neck of a user in a proper alignment position when the user is sleeping or resting on his or her side and opens airways of the user in a stable manner to promote easy breathing while preventing snoring.

The invention will now be described by way of example with reference to the accompanying drawings, in which.

Figure 1:
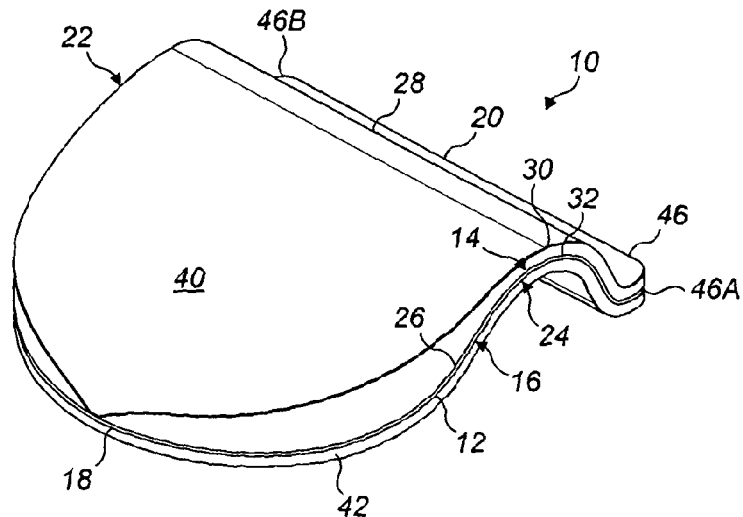
FIG. 1 illustrates a perspective view of an arm protector head rest according to the present invention.

As used herein, the term 'arm' is intended to include at least the hand and/or forearm.

As used herein, the term 'about' is interpreted to mean plus or minus 20%, more preferably plus or minus 10%, even more preferably plus or minus 5%.

With reference to the Figures, which show one specific embodiment of the arm protector head rest according to the invention, a head rest in its totality is indicated by the reference numeral 10. The head rest 10 comprises a spine member 12 formed from a single piece of sheet material having generally parallel side edges 22, 24, a front edge 18 in the form of a semicircle and a generally straight rear edge 46 with curved ends 46A and 46B. Suitable materials for the spine member 12 include semi-rigid or rigid, flexible plastics, such as acrylic polymer, metals, rubber, etc. The spine member 12 has a generally curved shape in cross section and has an upper surface 14, a lower surface 16, front and rear ends, 18, 20, and generally parallel side edges 22, 24. The upper surface 14 of the spine member 12 has a forwardly facing portion 26 and a rearwardly facing portion 28 that meet at the apex 30 of a convex portion 32. The upper surface 14 of the spine member 12 is formed with a slightly concave contour 34 in the generally forwardly facing portion 26 presenting a head support portion. This first concave portion 34 is resiliently flexible and flexes slightly into the passageway 36 when the weight of a user's head is applied thereto (see FIG. 3). A second concave portion 50 is provided in the rearwardly facing portion 28. Thus, the spine member 12 curves upwardly from the front and rear ends 18, 20, towards the passageway 36 forming the respective first and second concave portions 34, 50, in the upper surface 14. The radius of curvature of the first concave portion 34 is seen to be greater than the radius of curvature of the second concave portion 50. The front and rear portions 44, 48, of the spine member 12 curve upwardly from the resting surface 38 and flex under the weight of a user's head so as to be in contact with, or in the same plane as, the resting surface 38.

In the embodiment illustrated in the Figures, the spine member 12 has a width from one side edge 22 to the other side edge 24 of 432 mm and a thickness of 4 mm. The length of the head rest 10 from the front edge to the rear edge is 480 mm, or in an alternative embodiment is 530 mm.

A passageway 36 extends from one side edge 22 of the head rest 10 to the other side edge 24 and is of a height and width sufficient to comfortably accommodate two arms of a user side by side without impinging upon the circulation of either arm. In the embodiment illustrated in the Figures, the passageway 36 extends to a height of 105 mm above the resting surface 38. The length of the passageway 36 corresponds to the width of the head rest 10 and is 432 mm. The width of the passageway 36 is 412 mm, which reduces to about 232 mm when a user's head is applied to the head rest 10 due to the downward flexing of the curved portions of the front and rear ends 44, 48 (see FIG. 4). The reduced width passageway 36 remains sufficiently dimensioned to accommodate one or both arms of a user.

A first layer of foam material 40 covers the upper surface 14 of the spine member 12 and a second layer of foam material 42 covers the lower surface 16 of the spine member 12 to form a three layer construction. The first foam layer 40 has a lower density than the second foam layer 42 to provide a cushion feel on the upper surface 14 and a firmer more robust feel on the lower surface 16. The foam material 40 provided on the upper surface 14 of the spine member 12 is of a thickness of 58 mm at its thickest point in the head support or concave portion 34 and it tapers to a thickness of 13 mm at its thinnest points. The thickness of the foam material on the lower surface 16 of the spine member 12 is 13 mm. The foam layer 40 should be non-irritating to the human user and may be of varying firmness and resiliency to suit a particular user's taste.

Various known types of polymeric foam may be used to cover the spine member 12, including by way of example but without limitation, polyurethane foam, synthetic so-called foam rubber, latex foam, or visco-elastic foam commonly referred to as "memory" foam.

Figure 2:
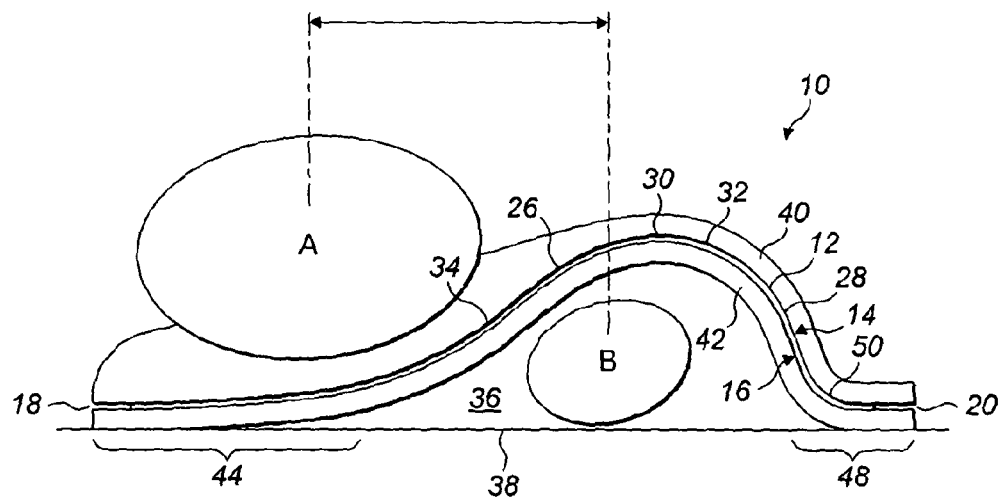
FIG. 2 illustrates a side view of the head rest of FIG. 1 showing the positions of a user's head A and arm B.

In FIG. 2, the oval shape marked "A" represents a user's head rested on the head rest 10 in a laterally side-facing disposition, and the oval shape marked "B" represents a user's forearm received through the passageway 36. It is clear from FIG. 2, that the head rest 10 is shaped so that the user's arm B may be positioned in the passageway 36 either tucked in close to the user's head A or away from the user's head A. Either way, the user's head is elevated relative to the user's arms but is not positioned directly above the user's arm. The unique curved shape of the spine member 12 therefore provides distinct portions for head support and place for arms.

Figure 3:
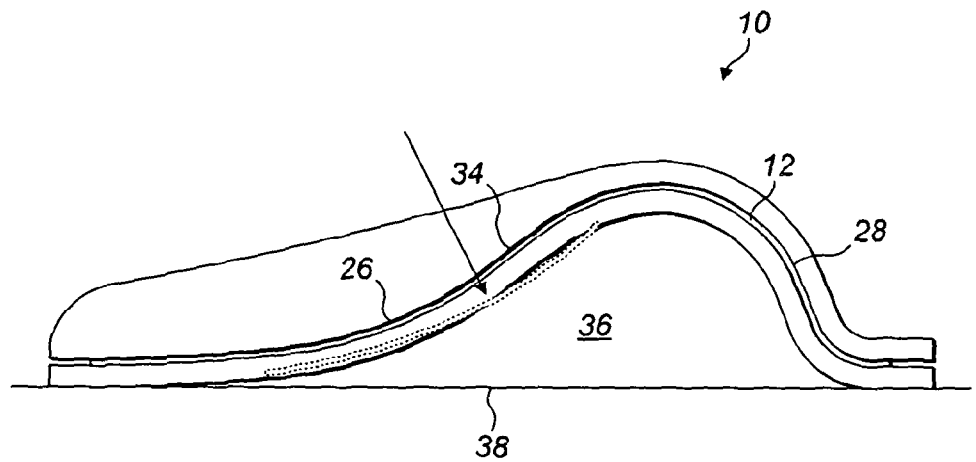
FIGS. 3 and 4 illustrate side views of the head rest of FIG. 1 showing the forces applied in use and the areas that are resiliently flexible.
Figure 4:
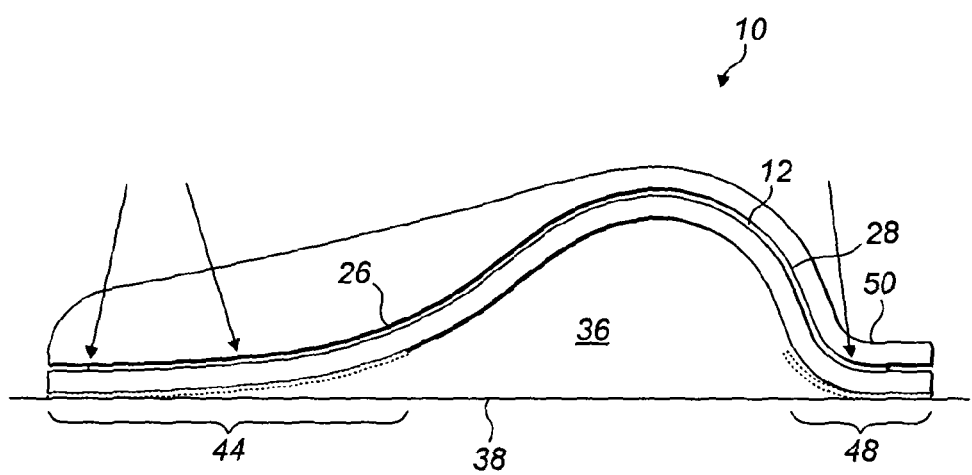

With reference to FIGS. 3 and 4, the areas of the head rest marked with dashed lines are configured to flex under the weight of the user's head. The shape and material of the spine member 12 ensure that a load applied to the head rest in use is distributed over a relatively large area to provide even stress distribution.

It is clear from FIGS. 2 to 4 that the unique shape of the spine member 12 achieves multiple functions. Thus, the spine member 12 allows the head of a user to be resting in an elevated position above the user's arms whilst providing a space for the user to place their arms away from the head; it provides structural integrity for a head support system, it separates two different densities of foam, the upper foam layer for comfort and the lower foam layer for durability; it allows slight flexing under the weight of the user's head for comfort and for even stress distribution; and ensures that the area of contact with the resting surface 38, which is most probably a mattress with a cover sheet, is large and flat, thereby reducing wear both on the mattress and the head rest itself.

With reference to FIG. 2, the head rest 10 according to the present invention provides support to a user's head and protection of a user's arm while allowing the neck to be relaxed. A user's head A may be rested on the head rest 10 in a laterally side-facing disposition while the user's arm B is received through the inner passageway 36 of the, or an adjacent, head rest 10. Alternatively, a user may lie on his or her front with his head rested on the head rest 10 in a laterally side-facing disposition and his arms received through opposite open ends of the passageway 36. Furthermore, the shape of the head rest according to the present invention encourages users to centre their heads on the forwardly facing portion 26 of the head rest 10 because the concave contour 34 of this portion of the head rest 10 makes them aware of when their heads are not centred on the head rest 10. This results in the correct positioning of head so that the head and neck are in a proper alignment position.

The foregoing description of a specific embodiment of the present invention has been presented for the purpose of illustration and description. It is not intended to be exhaustive or limit the present invention to the precise form disclosed, and variations and modifications are possible in the light of the above teaching. Therefore, the present invention includes all variations and modifications encompassed within the scope of the appended claims.

In this regard, it will be apparent to one skilled in this art that the head rest can be manufactured in a range of sizes to accommodate children, adolescents, and adults of varying sizes.

Further, it should be recognised that the passageway may be made larger for certain individuals, for example patients that have a broken arm in a cast, or body-builders with a greater degree of musculature around the arms. Thus, the actual shape and size of the passageway are not critical provided that it can comfortably accommodate one or two human arms of a user.

The invention claimed is:

1. A head rest comprising a spine member having an upper surface, a lower surface, and front and rear ends, the upper surface comprising a generally forwardly facing portion and a generally rearwardly facing portion, wherein the generally forwardly facing portion includes a first concave portion for receiving the head of a user, the front and rear ends are configured for contact with a resting surface and, between the front and rear ends, the lower surface defines a passageway dimensioned to receive at least one arm of the user, wherein the spine member has sufficient rigidity such that when the user's head is resting on the spine member, the at least one user's arm may be positioned in the passageway in a manner that does not require the at least one user's arm to support the weight of the user's head, wherein the generally forwardly facing portion and the lower surface of the spine member gently curve upwardly from the front end towards the passageway, the generally rearwardly facing portion and the lower surface of the spine member also curve upwardly from the rear end towards the passageway but at a greater angle than the front end in order to maintain the user's head and neck in a proper alignment position when the user is sleeping or resting on his or her side.

2. A head rest according to claim 1, wherein the front end of the spine member extends in the same plane as the resting surface.

3. A head rest according to claim 1, wherein a second concave portion is provided in the generally rearwardly facing portion.

4. A head rest according to claim 3, wherein the radius of curvature of the first concave portion is greater than the radius of curvature of the second concave portion.

5. A head rest according to claim 1, wherein the first concave portion is resiliently flexible and configured to flex when a user's head is applied thereto.

6. A head rest according to any one of claims 3 to 5, wherein the second concave portion is resiliently flexible and configured to flex when a user's head is applied to the first concave portion.

7. A head rest according to claim 1, wherein the rear end extends in the same plane as the resting surface.

8. A head rest according to claim 1, wherein the passageway is dimensioned to accommodate two arms simultaneously.

9. A head rest according to claim 1, wherein the spine member is made from moulded plastic.

10. A head rest according to claim 1, wherein at least the generally forwardly facing portion is covered with a foam material.

11. A head rest according to claim 1, wherein the foam material covers the entire upper surface of the wine member and is relatively thicker in the first concave portion than elsewhere.

12. A head rest according to claim 1, wherein the lower surface of the spine member is covered with a foam material.

13. A head rest according to claim 12, wherein the foam material on the upper and lower surfaces of the spine member have different densities.

14. A head rest according to claim 1, further comprising a fabric removable cover.

* * * * *

UNITED STATES PATENT AND TRADEMARK OFFICE
CERTIFICATE OF CORRECTION

PATENT NO. : 8,997,285 B2  Page 1 of 1
APPLICATION NO. : 14/235913
DATED : April 7, 2015
INVENTOR(S) : Philip Moore It is certified that error appears in the above-identified patent and that said Letters Patent is hereby corrected as shown below:

On the Title Page:

In the Assignees Item 73:

The name "Phillip Moore" should read "Philip Moore".

In the Claims:

Column 6, Line 54, the word "wine" should read "spine".

Signed and Sealed this
Twenty-fourth Day of November, 2015

Michelle K. Lee
*Director of the United States Patent and Trademark Office*